US009328337B2

(12) United States Patent
Geraci et al.

(10) Patent No.: US 9,328,337 B2
(45) Date of Patent: May 3, 2016

(54) ORGANIC, METALLORGANIC AND BIOLOGICAL MATERIAL OBTAINED FROM ROCK

(76) Inventors: Giuseppe Geraci, Giorgio a Cremano (IT); Bruno D'Argenio, Nappoli (IT); Rosanna Del Gaudio, Naples (IT)

(*) Notice: Subject to any disclaimer, the term of this patent is extended or adjusted under 35 U.S.C. 154(b) by 1467 days.

(21) Appl. No.: 10/543,292

(22) PCT Filed: Jan. 23, 2004

(86) PCT No.: PCT/IT2004/000013
§ 371 (c)(1),
(2), (4) Date: Jan. 31, 2006

(87) PCT Pub. No.: WO2004/065333
PCT Pub. Date: Aug. 5, 2004

(65) Prior Publication Data
US 2006/0134798 A1    Jun. 22, 2006

(30) Foreign Application Priority Data
Jan. 23, 2003    (IT) .............................. RM2003A0026

(51) Int. Cl.
*C12N 9/16*    (2006.01)
(52) U.S. Cl.
CPC . *C12N 9/16* (2013.01); *Y10T 436/25* (2015.01)
(58) Field of Classification Search
CPC ................................ C12N 9/16; Y10T 436/25
USPC ........................................................ 436/174
See application file for complete search history.

(56) References Cited

U.S. PATENT DOCUMENTS

| 4,280,002 | A | * | 7/1981 | Bailey et al. | ............... | 435/305.4 |
| 5,545,535 | A | * | 8/1996 | Roth et al. | ...................... | 435/34 |
| 5,902,742 | A | * | 5/1999 | Petter et al. | ............... | 435/252.1 |
| 6,358,700 | B2 | * | 3/2002 | Fumiyoshi et al. | ............. | 435/34 |

OTHER PUBLICATIONS

Geraci et al., "Microbes in Rocks and Meteorites: A New Form of Life Unaffected by Time, Temperature, Pressure", 2001, Rend. Fis. Acc. Lincei, S. 9 V. 12, p. 51-68.*
Steele et al., "Microbial Contamination of Allende and Murchison Carbonaceous Chondrites; Developing a Protocol for Life Detection in Extraterrestrial Materials using Biotechnology.", NASA, 2001.*

* cited by examiner

*Primary Examiner* — Jonathan Hurst
(74) *Attorney, Agent, or Firm* — Ferdinand M. Romano; Beusse, Wolter, Sanks & Maire, PLLC (57) ABSTRACT

The present invention concerns methods for obtaining from samples of rock of different natures, specifically chondrites, organic, metallorganic material or material of biological origin, and the materials themselves so obtained. In addition, the invention concerns their use in instrumentations exploiting their physical and physico-chemical properties, and fluorimetric methods to reveal such materials.

6 Claims, 8 Drawing Sheets

ORGANIC, METALLORGANIC AND BIOLOGICAL MATERIAL OBTAINED FROM ROCK

TECHNICAL FIELD OF THE INVENTION

The present invention concerns methods to obtain organic, metallorganic or biological materials from samples of rock of different nature and materials so obtained. The invention concerns also their use in instrumentations that employ their physical and physicochemical properties and fluorimetric methods for the identification of those materials.

STATE OF THE ART

It is known that crystals, rocks and minerals of different origins and compositions contain organic materials, in some cases of biological origin, as also viable micro-organisms capable of exiting from a quiescent state once freed from the rock structure and suspended in a suitable nutrient medium (Geraci et al., Rend. Fis. Acc. Lincei, s. 9, v. 12:51:68, 2001). These forms of life, when entrapped within the rock, are not influenced by time, as viable micro-organisms, suitable for cultivation, have been found in samples of rocks of different ages, tracing back to about 2.8 Ga (billions of years), and by temperature and pressure, since they are present in metamorphic and igneous rocks (Geraci et al, supra).

Research studies, with similar approaches, of microbial forms has demonstrated that also meteorite rocks may contain micro-organisms, indicating that these already existed during the initial stages of Earth formation. Some microbial species have been obtained in cultures, cloned and classified by the method based on the analysis of their 16S rDNA resulted not differing from the today micro-organisms. The method of extraction of biological materials described by Geraci et al. (supra) involves sterilization by flaming of relatively large rock samples for relatively brief flaming times (about 2 minutes), and then extraction from the most inner part of the sample, through series of drillings going deep about 10 mm, of small fragments of rock, which are then put in culture. Considering the sample size and the operative times, it cannot be excluded that the surface thermal treatment does not reach the necessary sterilization efficacy at a deep level. The doubt remains, however, that the viable life forms, apparently extracted from the rock structure, do not actually trace back to origin of the rock, but might represent environmental contamination occurred during the operative procedure or, in any case, in more recent times.

Scope of the present application is then that of providing a new procedure that enables the search, identification and study of organic materials of different origins, comprising materials of biological origin or viable micro-organisms entrapped inside the crystal structure of ancient rocks, eliminating the problem of false/positive results due to contamination of samples during the operational procedures or to any other type of recent contamination. Scope of the present invention is also that of demonstrating if, by applying the above mentioned procedure, organic materials, biological materials or even viable micro-organisms may be found in samples of rocks, or of ancient minerals of Ga of age or even in rocks of meteorite origin.

SUMMARY OF THE INVENTION

The method according to the invention entails a procedure of profound sterilization in alcohol and in a free flame and/or in autoclave for periods of time longer than these described in the state of the art. The method then implies the production of rock fragments directly from the surface of the sample, that is from the part where the heating sterilization procedure is expected to have been most effective. Hence, the procedure permits to eliminate the presence of any organic or biological material deriving from possible environmental contamination of the sample under examination and to put in evidence, through suitable means, the presence of organic or biological materials pre-existing in the very structure of the rock and protected by this against the destructive effect of the heating treatment. The method has permitted to demonstrate surprising results.

Accordingly, the object of the present application is a method for obtaining from samples of rocks of different origins, but in preference from chondrites, organic, metallorganic or biological materials, this method comprises the treatment of the rock sample at sterilizing temperature for at least 5 minutes. Then, fragments of the sterilized sample are produced by means of a mechanical treatment of the sample surface and put on a sterile solid nutrient culture medium based on hydrolyzed natural products or synthetic derivatives thereof, either in the presence or in the absence of oxygen at room temperature. The material generated on the surface of the fragments is then separated from the fragments, isolated from the solid culture medium and optionally further elaborated. The sterilization step is performed by dipping the sample in alcohol and subsequently treating it directly on a flame for at least five minutes.

Further object of the invention are the materials obtained by this method in the presence of oxygen; preferably obtained from chondrite samples. These latter materials are characterized by an iron contents bound or complexed to organic molecules, and comprising mixtures of saccharides and N-acetylaminosaccharides in defined ratios. The generation of such materials on the surface of chondrite fragments occurs through an initial developmental stage in which the material is organized in pigmented globular vesicular structures containing or not a fluid, followed by a phase of quiescence in which the material is organized in globular structures, rigid and highly pigmented, open or closed, showing a positive geotropism. The wall of these structures, that is formed by repetitive units rich in iron and by thin membranes without iron, exhibits unexpected and surprising physical and physico-chemical properties such as an exceptionally strong capacity to absorb light energy and magnetic properties. Moreover, the globular vesicular structures containing fluids, when disaggregated in solution and labelled with a fluorescent marker for nucleic acids, show the presence of fluorescently labelled entities of size smaller than a micron, with very peculiar structure and endowed of a pulsating mobility.

Further object of the invention are methods for identifying by fluorescence nucleic materials comprising the organic, metallorganic and/or biological materials obtained according to the described method.

Other objects of the invention are technical elements, such as sensors or control elements, that include the above described material, and make use of their absorbing or energy-dissipating or magnetic properties.

These elements are parts integrated in instrumentations receiving, absorbing and utilizing energy, or instrumentation for magnetic or optical orientation, that also are objects of the invention.

Finally, objects of the invention are the use of these structures or of their composing parts or of materials obtained from them, as catalysts in chemical reaction.

BRIEF DESCRIPTION OF THE FIGURES

FIG. 1: The figure shows the types of structural shapes that are generated from fragments of iperstenic chondrite incubated in sterile Petri dishes. Panel (a): club-shaped structures at initial growth stages (about 12 hours incubation) that can be seen on the fragments 1 and 3. Panel (b): same area shown in Panel (a), after about 1 month; it is possible to recognize the initial structures increased in size and complexity and a new structure on fragment 2. Panel (c): wall of a structure at a growth time in which there are evident the modular elements that constitute it and, in the adjacent panel, an enlargement of the indicated area. Panel (d): aged structure that has divided into two valves showing in the interior, where the valves are joined, a mass of small globular objects embedded in a refracting matrix. Panel (e): aged structure with a form of a bell-shaped corolla. Panel (f); an aged structure with a hemispherical shape. Panel (g): the same fragment as shown in panel (f), showing a new structure in formation at the stage of hyper refractive transparent bubble, two weeks after the mechanical removal of the previous one for analytical studies. Panel (h): micro photograph of the wall of a structure in which modular, highly pigmented elements are evident.

FIG. 4: The figure reports images obtained at the scanning electron microscope. Panel (a) shows details of the wall of opened structures with a cup-shaped form (bell). The wall is composed of a complex organization in layers and modules. Enlargement 1*a*, shows spherical bodies of about 0.4 microns comprised in the interior of the wall. Enlargement 2*a* shows details of the repetitive units that compose the same wall. Panel (b) shows other details of the repetitive elements and thin membranes that form the wall. Panel (c) shows thin structures in tight packing characterized by slightly curved filamentous protrusions departing from conical bases. Panel (d) shows wide, hollow, globular wall elements ranging in size 30-40 micron. On the inner surface of such globules, elements of different morphology can be observed (as reported in panel (e) and enlargement), such as clusters of rod-shaped objects resembling bacterial cells and minute star-shaped bodies.

The upper panel shows a general picture of a dish; the three lower panels show details of cavities where the presence of fragments of a structure of the invention can be noted at the extreme progressing part of a cavity. Observation made from the inferior side of the culture dish where the upper surface is on the opposite side.

DETAILED DESCRIPTION OF THE INVENTION

Crystals, rocks and minerals of different origins and ages contain organic and biological materials, including viable micro-organisms.

The method described in the present application permits to identify and to obtain such materials from rock samples of various origins minimizing the risk of environmental microbiological contamination. Examples of samples of rocks are metamorphic, igneous, sedimentary, mineral rocks or marine sediments obtained from different depths, these latter representing the precursors of such rocks, or, also chondrites, octahedrites and rocks of similar origin. Preferably the method is carried on iperstenic chondrites or enstatitic olivines.

The method implies that the samples be exposed to a sterilizing treatment at high temperature. Suitable methods are the heating in a kiln, or in autoclave or direct exposure to microwave oven or to the flame of a burner, as for example a Bunsen. The combination of a treatment in autoclave, preceded or followed by direct exposure to the flame, is the preferred procedure. Nonetheless, a preliminary treatment with alcohol or other sterilizing solvent, offers even more assurances that any environmental biological contamination is eliminated. In this case the sample, still wetted with solvent, is directly put in the flame of the burner.

The time of exposure to the direct flame is of not less than 5 minutes. Longer times, for example, 10, 15 or 30 minutes, may nonetheless be utilized. The treatment times in autoclave vary between 20 minutes and 2 hours, though longer times may be envisaged.

The surface of the so treated sample is fragmented in pieces not larger than 1 mm, by grinding with a suitable drill, scraping with suitable file or other similar tool, or excavating with a syringe needle or any other sufficiently hard acuminated tools. These operations are performed under a strictly sterilized atmosphere, operating with previously perfectly sterilized instruments. Fragments so obtained are deposited on a solid nutrient medium based on hydrolysates of natural products or their synthetic derivatives, or mixtures of their components, also synthetic, such as tryptone, yeast extracts, agar. The preferred culture medium contains for 1 g. of tryptone (Oxoid), 1 g. NaCl, 0.5 g of yeast extract (Oxoid) and 1.4 g of Bacto Agar (Difco) in 100 ml of water.

A second culture medium is the product of gelrite gellan Gum® (Sigma-Aldrich), that is a natural agent substituting agar, composed of glucose units, glucuronic acid and rhamnose, used in microbiology and for plant cultures at the following conditions: 0.8% gelrite gellan Gum® in growth medium DSM-182, in Petri dishes, at pH 4.0 or in growth medium TYS at pH 3.2, respectively; incubation at room temperature for 2 or more days.

Mixtures of combinations of hydrolysates different from these, but equivalent, having various origins, also made by mixing pure components, are equally valid, although more expensive.

The preparation conditions of the culture media as well as the culture conditions are critical. The above indicated culture media are heated to boiling point to solubilize agar or gelrite, are sterilized for 20 min in autoclave at 121° C., and stored for at least one month to be sure that there are no residual contaminations. Before use, the solid culture medium is heated to melt it and is dispensed in requested amounts, for example about 20 ml, in each standard Petri dish (90 mm diameter), that is then sealed and cooled producing the gelification of the culture medium.

In order to obtain the structures described below, an essential culture condition is the presence of oxygen. Anaerobic conditions do not normally produce the described results.

While the method before described by Geraci et al., (supra) permitted the identification of viable micro-organisms already known in samples of differing ages, starting from 2.8 Ga back, the method of the invention, applied to samples of chondrite material, has permitted to obtain completely unforeseeable and unexpected results.

In a preferred embodiment of the invention, the method is performed on types of iperstenic chondrites classified L6. Two of these types, Mocs and Holbrook, conserved in different museum collections, have been chosen because they are parts of two seen meteorite swarms, fallen in distant areas of Earth, at different climatic conditions, and because they remained for short time on the soil before their collection and conservation in different museums collections.

When fragments obtained according to the method of the invention, having diameters of less than 1 mm, are put on a solid nutrient medium and incubated for a period of 5-7 hours, at room temperature and in the presence of oxygen, on their surfaces it is observed the generation of materials formed through a developmental phase followed by a phase of quiescence. In the initial phase, the material is organized in small globular blobs, as liquid vesicles or containing liquid, with a pigmentation ranging from pale amber yellow to orange or red, from pale to deep ruby, anchored to the black fragments of iperstene (FIG. 1a).

Figure 1:
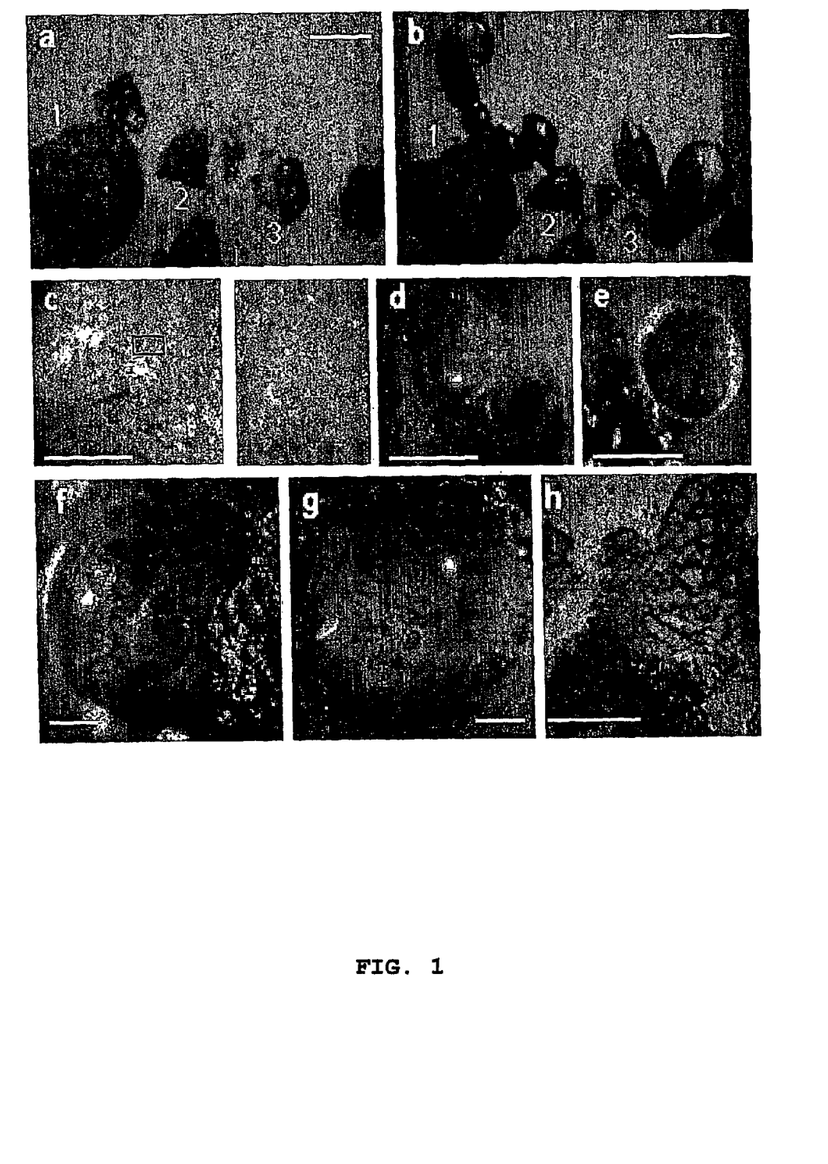

After longer incubation times, other structures grow out that, in a period of one, two, three or more months, increase in size and structural complexity becoming dark orange or deep red, with a growth that shows a positive geotropism (FIG. 1b). The size of the structure is frequently larger than that of the fragment from which it is generated.

The globular structures, observed at an initial phase, show a great transparency and an elastic fluidity of the wall comparable to that of a soap bubble. Pigmented material initiates to form on the external surface of the fluid globe and in time it expands to the entire surface. The transparent liquid initially present is no more observed in the structures at advanced stages or in a quiescent state that acquire a quasi-crystalline appearance formed by modular units (FIG. 1c and related enlargement). This type of development has been observed in almost 500 structures in a period of almost 2 years.

The structure, initially with a vesicular shape, may assume with development a typical club-like form. Property of these club-like structures is that of responding like a magnet to an external magnetic field, if mechanically detached from the fragment from which they had been generated. After a period of a few months of incubation, the structures enter an apparently quiescent state, in which their form does not change in a period of at least one year.

Three are the most frequently observed forms of the structures at the end of their growth and these depend on the structure initially presented. To a first type, all the structures belong that have a club-like form and that during development may divide along a meridian, forming two valves united at the base, where a mass of small globular bodies is present embedded in a transparent, highly refractive matrix (FIG. 1d). In a second type of structures, the upper spherical part of the club-like form opens up producing a sort of reversed bell-shaped corolla that shows at the bottom, a complex aggregate of small spherical bodies (FIG. 1e). Finally, the structures maintaining during aging the hemispherical form lose their refractive aspects of the liquid layer and assume a quasi-crystalline highly breakable form (FIG. 1g). If this type of structure is mechanically removed from its site of formation on the fragment, a new one is formed with properties similar to the pre-existing structure through an initial stage in which a transparent and highly refractive liquid layer is formed again, and this in time is gradually inflated becoming hemispherical (FIG. 1g). On this layer, then, the highly pigmented parts are produced, which initially seem to freely float on the surface of the liquid layer. This regeneration may occur several times.

The material that forms the above described structures in the various phases of their development or parts of them, when analysed by direct analytical methods that minimize the possibility of erroneous attributions, presents completely unexpected reproducible physicochemical characteristics, having interesting industrial applicability.

A first property of the structures, in the phase characterized by the typical club-shaped form, is that to respond like a magnet to a magnetic external field, if mechanically detached from the fragment from which they were generated. Another surprising property is the enormous capacity of the wall of aged rigid structures to absorb light energy. This property is deduced by the practical impossibility to measure reflection spectra, using a Zeiss micro-spectrophotometer, in the wavelength region from 280 nm to 800 nm, because the quantity of reflected energy is insufficient for any reliable recording.

Figure 2:
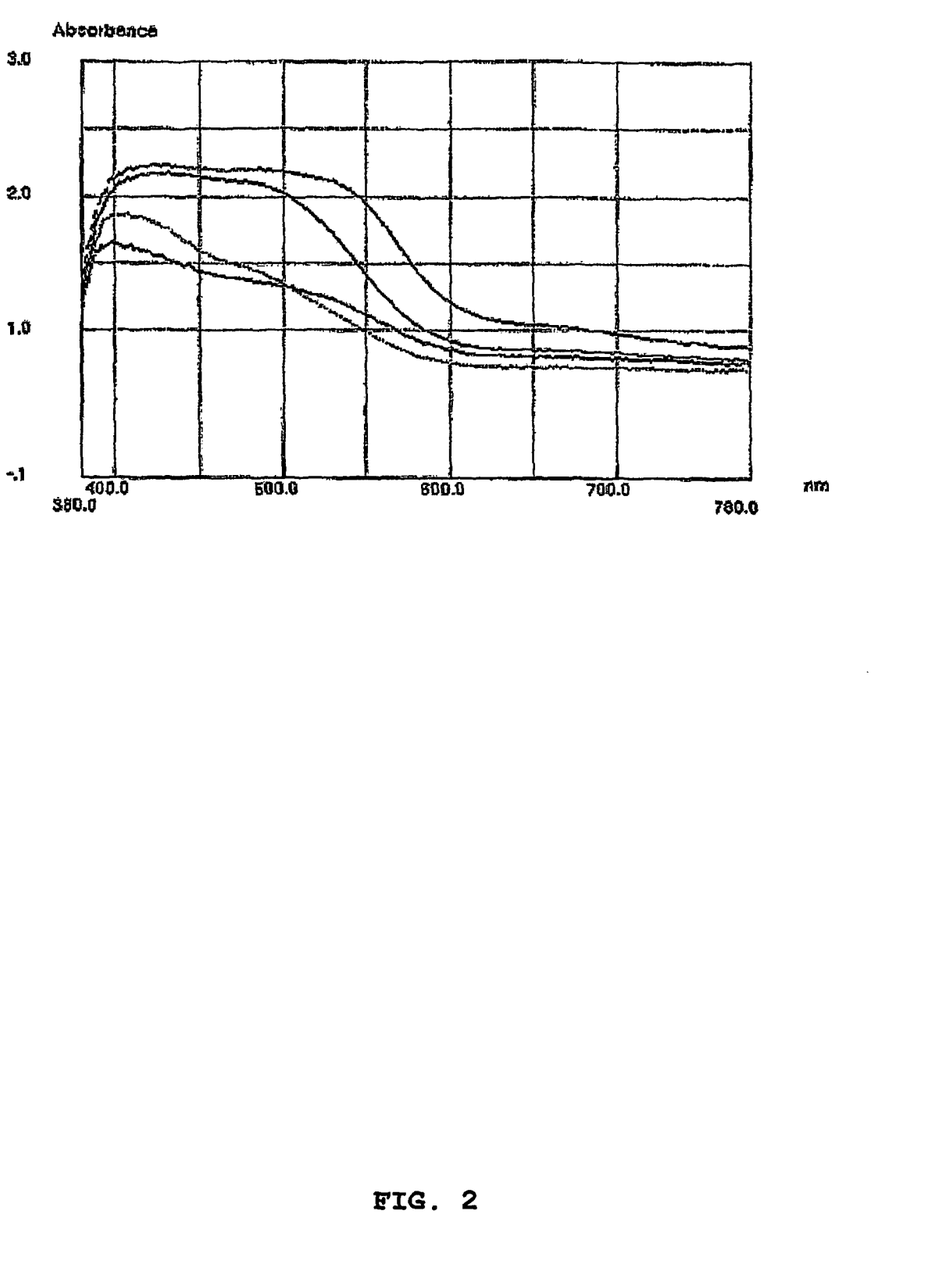
FIG. 2: The figure reports visible absorption spectra obtained with a Zeiss micro spectrophotometer. The different spectra correspond to different zones of the iper-pigmented fragments shown in FIG. 1*h*. Magnified 1000×. The spectra show decreasing absorption at increasing wavelengths values, with a maximum of absorbance at 670 nm. The spectra show other bands of absorption at 530 nm, 488 nm and 404 nm.

Moreover, microspectrophotometric analysis in the visible range of light, performed directly on the fragments of the aged structures (like those of FIG. 1h) show the presence of multiple absorption bands. That at the longest wavelength, 670 nm, has the lowest extinction coefficient. Other bands of higher intensity are observed at the wavelengths 530 nm, 488 nm, and 404 nm. The absorption spectrum, in general, depends on the area of the fragment sampled by the micro beam (FIG. 2). The pigments responsible of such absorption bands are not present in the culture medium and can only derive from a synthetic activity peculiar of the structure itself. If a pigmented structure is treated with 2 M HCl, the structure and the red colour is destroyed in a few hours and the acid solution becomes yellow, as it is typical of ferrous salts in HCl. Since the spectra show multiple absorption bands, which do not correspond to those of hydrides or iron oxides, which monotonically increase in absorption at decreasing wavelength, the spectra indicate interactions between iron and organic molecules, such as in complex or chelation products. The structures' spectrum was determined directly by infrared analysis (IR), compressing the fragments in a diamond micro cell. During this analysis it is noted that the fragments do not fuse together, but instead they remain distinct, unlike rock materials. Spectra obtained by Fourier transform clearly show the presence of organic materials and, particularly, the resonating frequencies of the amide bond, but no clear presence of proteins. The chemical nature of the amide bond resulted to be that of N-acetyl-glucosamine by GC-mass spectroscopy performed on a single structure, by comparing the results to those obtained on a corresponding quantity of the culture medium.

The structure has shown the presence of Glucose, Galactose and N-acetyl-glucosamine. The relative ratios between these molecules, although somewhat variable, is essentially about 3.2:6.3:0.5. This ratio between Glucose and Galactose is different from that of the culture medium that contains Galactose and Glucose in a ratio of about 8:2, and does not contain N-acetyl-glucosamine. Since the culture medium does not comprise N-acetyl-glucosamine, it can only derive from organic material generated on the surface of the fragments.

The amplification of genetic material, such as rDNA, by means of PCR on the aged structures failed to give significantly positive results, indicating either that the genetic material is no constituent of the structures or that it is shielded, or also that the oligonucleotides used as primers, not being the suitable ones, found no binding sites. On the contrary, on young vesicular structures, still in a fluid form, bands of DNA are obtained by PCR amplification using standard oligonucleotide mixtures aimed at amplifying rDNAs of eubacteria, archea and animal, as described in the literature (DeLong, E. F. Archea in costal marine environments. *Proc. Natl. Acad. Scie. U.S.A.* 89, 5685-5689 (1992)) and of plants (Aceto, S., Caputo, P., Cozzolino, S., Gaudio, L. and Moretti, A., Phylogeny and evolution of Orchis and allied genera based on ITS DNA variation: morphological gaps and molecular continuity. *Mol. Phyl. Evol.* 13, 67-76, (1999). However, two cycles of amplification have been necessary to obtain weak and still non conclusive signals. The results are reproducible for each analyzed structure, but always show more DNA bands. Due to the scarce quantity of available starting material that requires repeated amplification cycles, the obtained data need confirmation and it is not possible as yet to make a definitive genetic identification. Although not wishing to bound the invention to specific theories, the observed results seem to indicate that more than one biological form participates to the formation of the described structures. This seems to be in agreement with the results of scanning electron microscopy (SEM) reported below that show a great complexity of structural organization.

Figure 3:
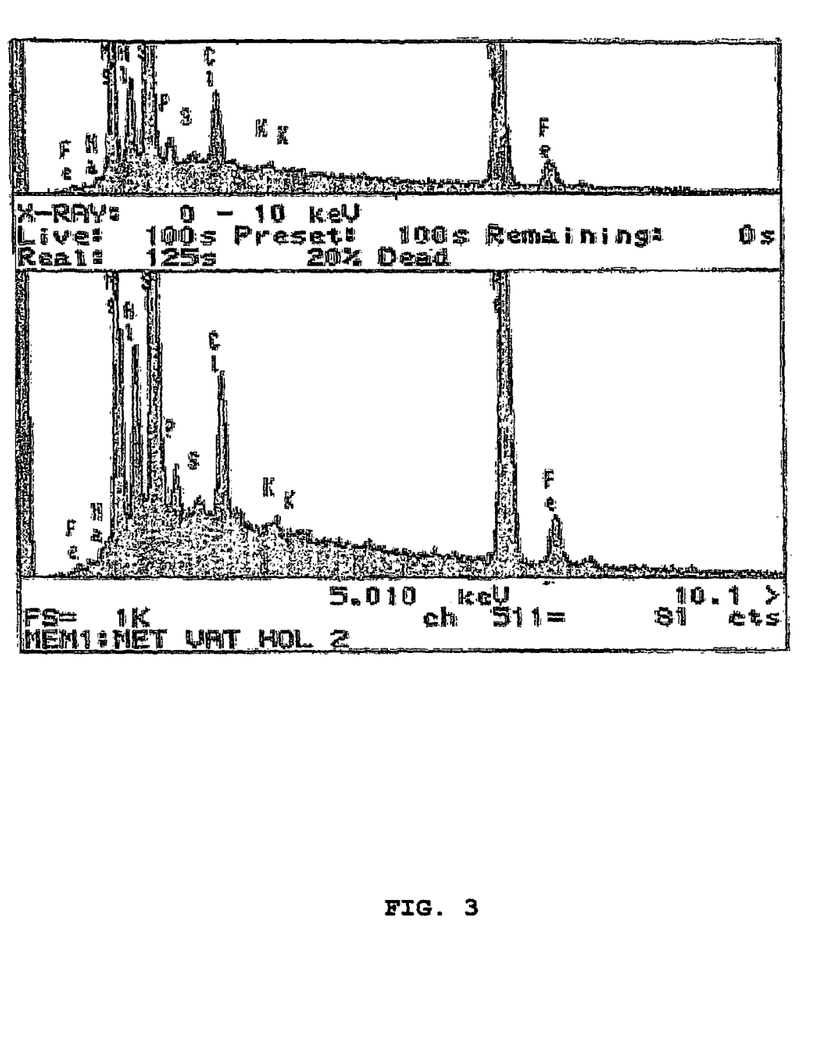
FIG. 3: The figure shows the results of the analysis of x-ray energy dispersion spectra (EDS) on samples of fragile, aged, pigmented, globular structures. The analysis shows iron as a most prominent metallic component.
Figure 4:
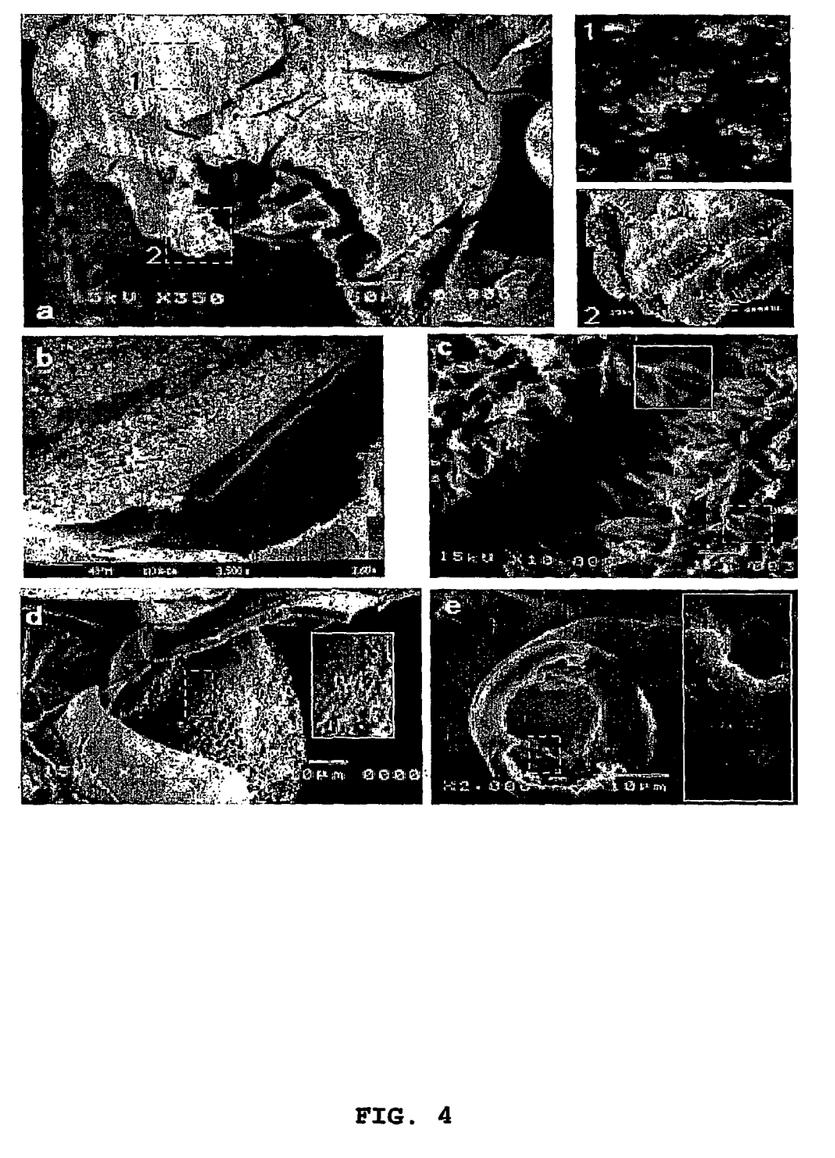

Spectroscopic microanalysis by X ray energy dispersion (EDS) performed at the SEM on the fluid material initially present in the structures shows the presence of atoms normally present in organic molecules and absence of metals. The same type of analysis performed on highly pigmented structures shows the presence of iron as sole metal (FIG. 3), and absence also of calcium. Hereinafter there are reported only the most relevant characteristics and details of the analysed structures. The SEM pictures show that the corolla shaped structures have a complex organization in modules and layers (FIG. 4*a*). In the magnified area 1, spherical formations of about 0.4 micron in diameter are observed inside the wall. The area of enlargement 2 of FIG. 4*a* shows more details of the repetitive structures already apparent in FIGS. 1*c* and *h*, by optical microscopy. A peculiar characteristic of these repetitive units is their brush-like surface. It is interesting to note that a very thin layer (FIG. 4*b*), which does not show metal components by EDS analysis, seems to be that organizing the pigmented, discrete, iron-rich units, that constitute the walls of the structures. This thin layer is probably what remains of the fluid hemisphere initially observed in the structures while just forming (FIG. 1*g*), on which the pigmented parts later on appear.

An enlargement of a fractured part of a wall shows the presence of very small structures, tightly adjacent each other (FIG. 4*c* and enlargements). The site reveals, by SEM analysis, the presence of thin appendages containing iron (EDS analysis) that are delicately curved and bound to the base of conical structures. Observation of other parts of the walls interior shows the presence of other components of different morphology, such as clusters of small rods (FIG. 4*e* and enlargement), that resemble bacterial cells and other sub-microscopic star-shaped bodies inside other hollow globular structures having 30-40 micron diameter (FIG. 4 and enlargement).

The present invention concerns also methods of fluorescence microscopy for identifying biological material or viable forms extracted from the samples of chondrites here described. The material is disaggregated in physiologic solution directly on a microscope glass slide and labelled with a solution used to fluorescently label nucleic materials. The labelling is specifically performed with a fluorophore that discriminates live from dead bacterial cells.

Figure 5:
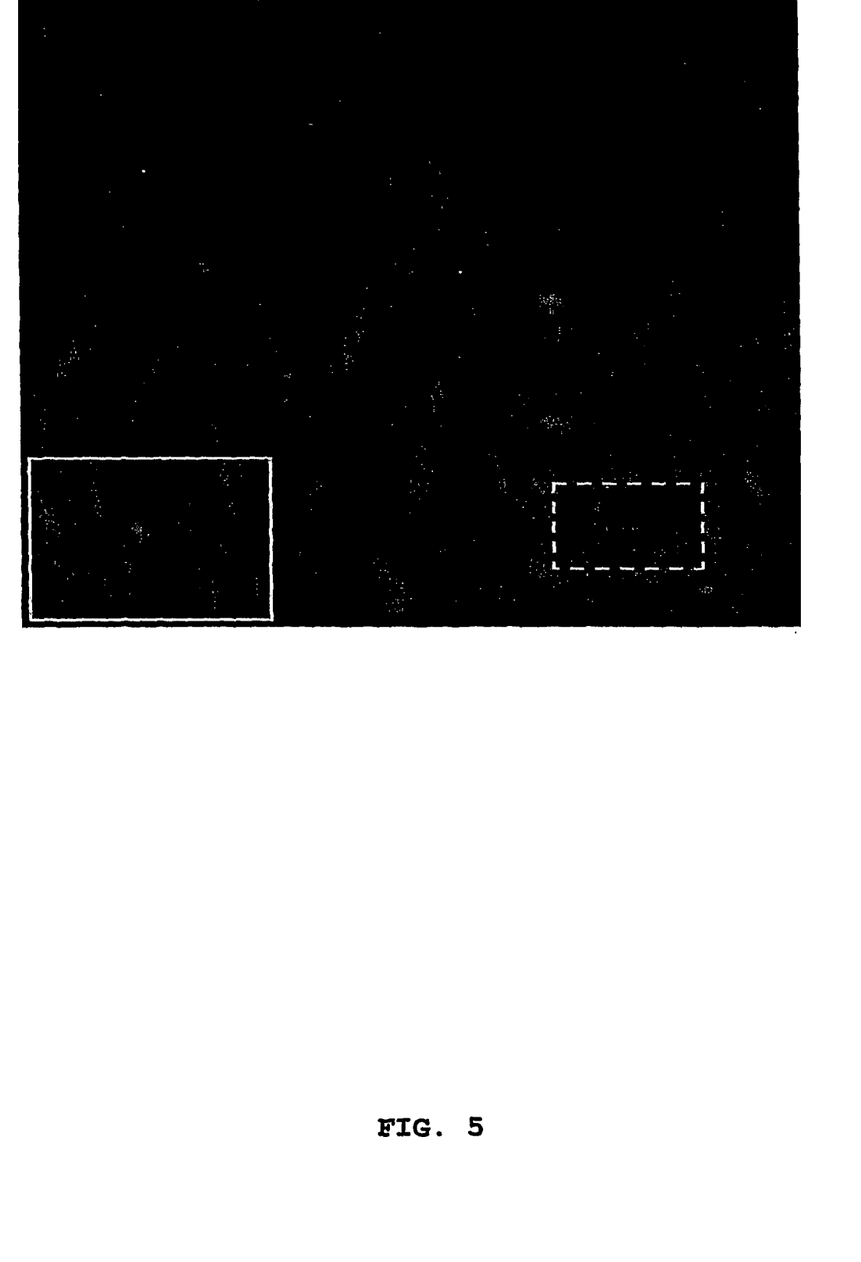
FIG. 5: The figure shows pictures in fluorescent light microscopy of globular vesicular structures at initial stages still containing liquid, disaggregated in physiologic saline solution directly on a microscope glass slide and then labelled. Scattered fluorescent spots of about one micron in diameter are observed, some of which, smaller and with starshaped structures, show motility in a pulsed gait (enlargement).

The observation is finally performed at the fluorescence microscope with suitable filters. This technique has been applied to the globular vesicular structures still in a fluid state. Typically, a structure is suspended in 30 microliters of sterile culture medium without agar on a glass microscope slide. The sample is then disaggregated by crushing with the needle of a sterile syringe. A suitable quantity (usually 1 microliter) of fluorescent label SYTO (3.34 mM) (Molecular Probes Inc.), or other equivalent reagent, is added under accurate stirring and the sample is incubated in the dark for at least 15 minutes. The analysis at the fluorescence microscope reveals the presence of several fluorescent immobile spots, of about 1 micron in size, and slightly smaller other ones, with multiple appendages similar to small gel fish (FIG. 5), showing halting movements. The shape of such objects (enlargements FIG. 5) has similarity with that shown in the enlargement of the units that compose the interior of the wall reported in FIG. 4*c*. It has not been possible yet to put in culture these entities for their further characterization.

As seen above, the handling conditions of the fragments on the culture medium are critical: cultivation occurs on a solid medium, all nutritional components are necessary, it is necessary to work in oxygen atmosphere, in fact, in anaerobic atmosphere no formation of structures is observed. On the contrary, as soon as anaerobic conditions are discontinued, in the period of few hours the structures appear in the culture. Exposition to UV light of the cultures with the chondrite causes inhibition of the growth. Only the formation of small clusters of little pigmented bubbles is observed, like small aggregates of foam, with no further growth.

Although without wishing to bind the invention to a specific theory, the presented data seem to indicate that the peculiar structures, which grow exclusively out of fragments of iperstenic chondrite meteorites, show physico-chemical characteristics peculiar of vital forms. There are some similarities with some properties of *Magnetospirillum magnetotacticum* for the sensitivity to magnetic fields. Yet, *M. magnetotacticum* produces chains of magnetosomes, magnetic crystals of iron oxide, with no resemblance with the morphology of the structures here presented for size, form and complexity of organization. There is also a certain similarity with the form shown by Mixobacteria in conditions of starvation, that is a spheroid, that however has no particular structure and does nor develop. Moreover, mixobacteria are easy to cultivate and have a large DNA genome. Furthermore, as already mentioned, the structures according to the invention show a positive geotropism and a complex structure with at least three distinct layers of components discriminated by SEM. This is probably the origin of multiple bands of amplification of rDNA by PCR that has not yet permitted the genetic characterization.

A particularly interesting property is the capability of the structures here presented to grow from fragments that have been exposed to the sterilization with alcohol, to flaming and to the subsequent keeping for 5 minutes in the flame of a Bunsen burner. When chondrite fragments that have been kept in a growth medium of E. coli (as an example of Gram negative bacteria) or of B. subtilis (as a an example of Gram positive bacteria) for 7 days, no bacterial growth has been observed from them after this type of sterilization procedure. The growth has instead occurred of the pigmented structures and of the fluorescently labelled forms above described. The possibility that heat has not reached the analysed parts is not tenable considering that the fragments are less than 1 mm in size and the time in the flame is 5 minutes. If the structures derived from some form of environmental microbiological contamination, this could not derive from the museums where samples were stored or from the laboratory environment. In fact, the structures develop from all samples of two different meteorite swarms fallen in different years in different environments such as Transylvania and the desert of Arizona stored for more than a century in three different museums in different parts of the world. The hypothesis of laboratory contamination is not realistic because the search of similar structures from rock samples and minerals of terrestrial origin, from sedimentary rocks to purified iperstene, has produced no similar result, as also the intentional massive contamination produced with Gram positive and negative bacteria has not resisted to the sterilizing treatment. Hence, if the structures are produced by contaminating terrestrial micro-organisms, the contamination should have occurred either before or during the fall on Earth, or while meteorites were lying on the soil. In this case, the contaminating form should be present in all environments and abundant to colonize in short time samples of meteorites fallen in so different environments (Agricultural soil of Transylvania and the desert of Arizona) in different years. Even in this case, the contaminating organism should have found a nutrient necessary to its growth in the meteorite considering that it does not grow from any terrestrial sample, and moreover, it should have established with the meteorite very peculiar relation that enabling it to resist both to the extreme sterilization conditions employed in the experiments here presented and to the time (at least one century) of conservation in the museums collections.

Due to the physico-chemical properties proper of the materials described here, these find applications in technological areas of importance.

In particular, the specific properties of absorbing light energy are utilized to prepare absorbing or dissipating materials or sensory elements, that can be integrated into instruments made to receive, absorb or utilize energy, specifically light energy. Moreover, the magnetic properties also may be used for the preparation of control elements integrated as components into instrumentations for magnetic or optical orientation.

Figure 7:
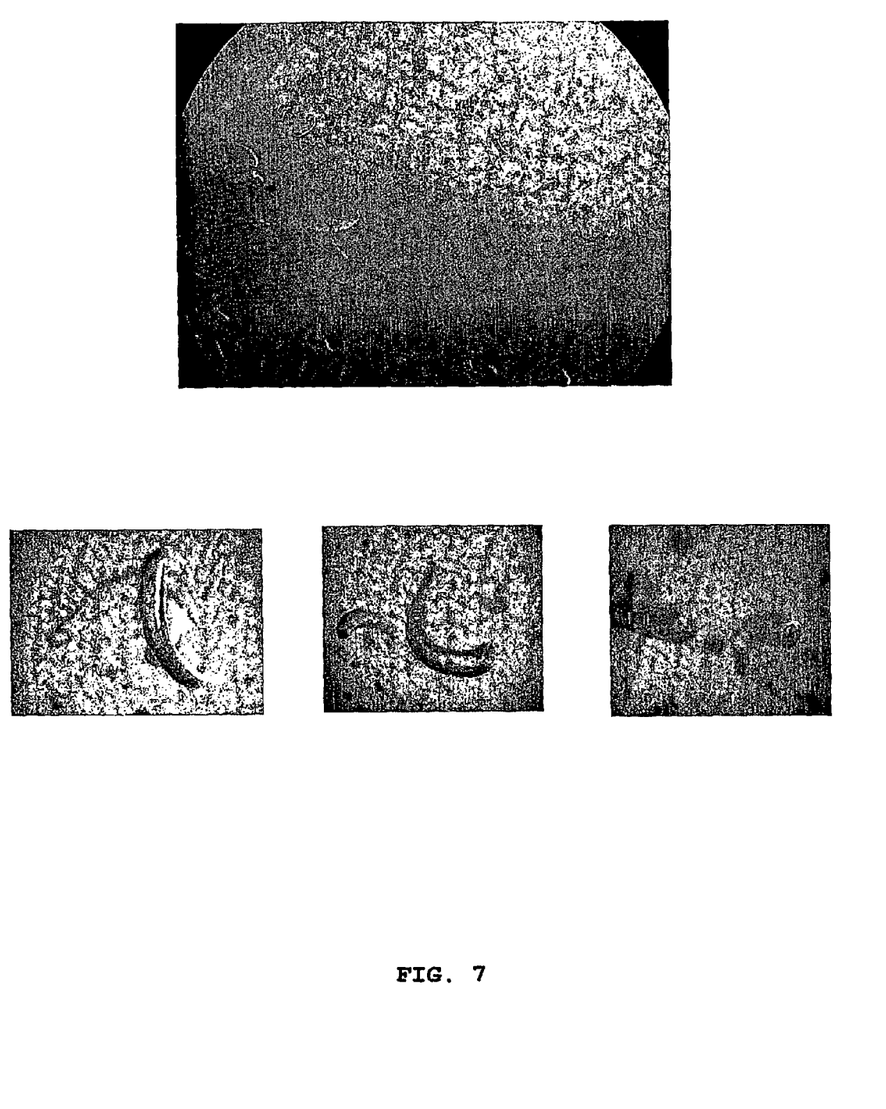
FIG. 7: The figure shows at binocular microscope the glycosylase activity of the fragments of the materials of the invention; these fragments generate hollow tubular cavities produced by the hydrolysis of the gelrite gellan Gum® (Sigma-Aldrich), that is a natural agent substitutive of agar used in microbiology and to cultivate plants in the following conditions: 0.8% gelrite in DSM-182 medium, in Petri dishes at pH 4.0 or 0.8% in TYS medium at pH 3.2, respectively; incubation at room temperature for 2 or more days.
Figure 8:
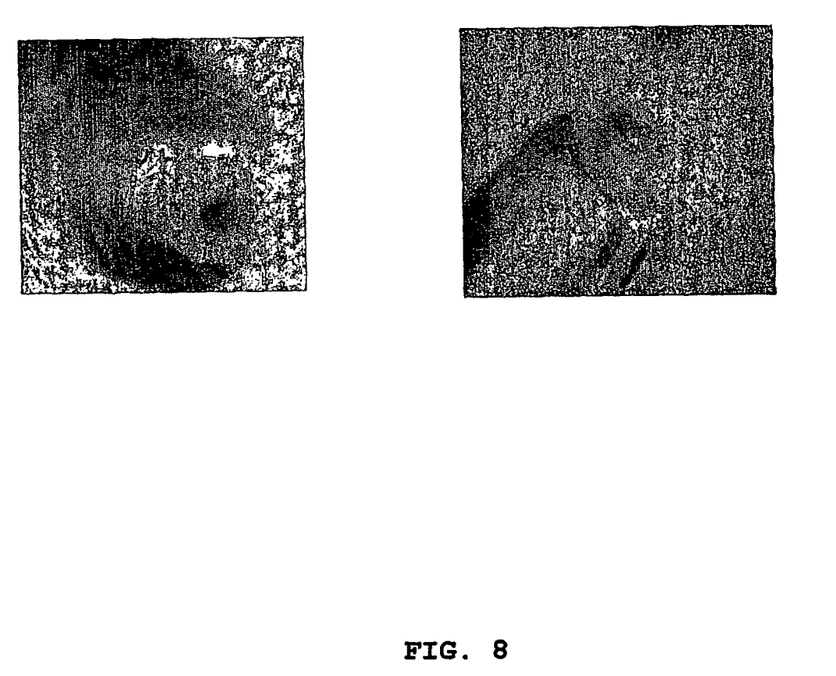
FIG. 8: the figure shows two enlargements of fragments that have produced the tubular cavities reported in FIG. 7.

It has been finally observed that the structure herein described o their parts or materials obtained therefrom produce a catalytic action on some organic chemistry and biochemical reactions such as hydrolysis and formation of ester bonds, of peptide bonds or glycosidic bonds. As shown in FIG. 7, the glycosylasic activity of the materials of the invention is well evident, on culture dishes, from the formation of hollow tubular cavities in the width of the solid culture medium in correspondence to fragments of the materials.

These hollow tubes are the result of the hydrolysis of the glycosidic bonds of the polysaccharides that compose the culture medium, such as gelrite gellan Gum® (Sigma-Aldrich).

Figure 6:
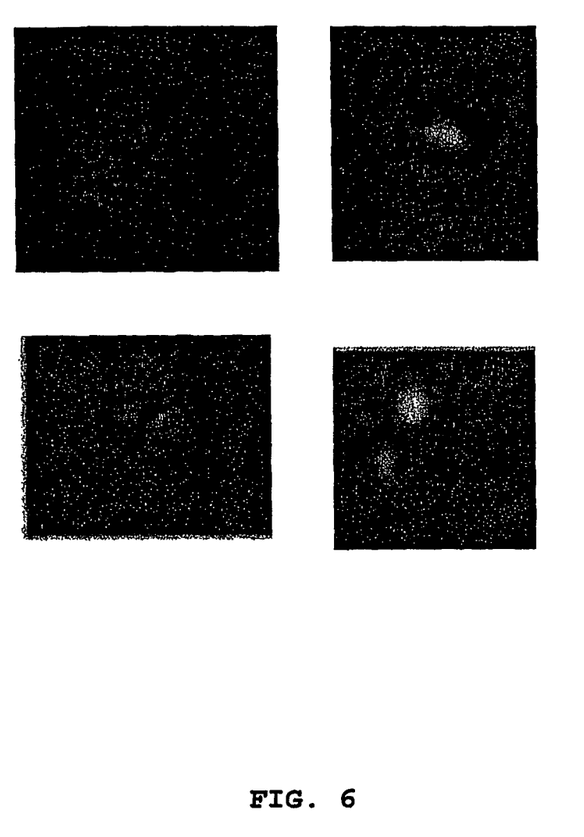
FIG. 6: The figure shows pictures in fluorescent light microscopy, of parts of the structures reported in FIG. 1, disaggregated in physiologic saline solution directly on a microscope glass slide and then treated with LB nutrient solution and carboxyfluoresceine diacetate ($H_2CFDA$, Molecular Probes). The green fluorescence that is observed after incubation at 4° C. for at least 15 minutes in the dark, is due to the hydrolysis of the acetyl residues from the carboxy fluoresceine, caused by aspecific esterase activity present in the fragments of the structures shown in FIG. 1, that become, for this reason, fluorescent.

The esterase activity may be put in evidence at the microscope in fluorescent light as shown in FIG. 6. The material of the invention, when in contact with carboxyfluoresceine diacetate (H2CFDA), produces the hydrolysis of the acetyl residues and the activation of fluoresceine with the production of the typical green fluorescence that is observed after incubation at 4° C. for at least 15 minutes in the dark.

Finally, the catalytic activity for the formation of peptide bonds is evidenced by the capability of forming oligopeptides or polypeptides in the presence of mixtures containing the 20 amino acids present in the culture medium. In fact, although in the structures of FIG. 1 no free amino acids are revealed by analytical procedures, analyses performed after acid hydrolysis reveal the presence of amino acids, but with ratios completely different with respect to those present and determined in the growth medium. This indicates that molecules with peculiar selections of amino acids linked to each other by peptide bonds are formed and present in the structures.

The invention is described below by means of a practical example.

Example

The Mocs and Holbrook iperstenic chondrites here analysed are parts of samples fallen, respectively, on 3 Feb. 1882 in Transylvania near Cluj (Mocs) and on 19 Jul. 1912 in the Arizona Desert in Navajo County, near Holbrook, both classified as ordinary chondrites L6. A fragment from Mocs and one from Holbrook have been obtained from the Real Museo Mineralogico of the University of Naples (Italy) and from the collection of the Vatican Observatory of Castelgandolfo (Italy). Another Mocs fragment has been a gift from the collection of the Eötvös Museum of the University of Budapest. Each sample has a precise identification in the catalogs of the museums and is certified.

Preparation of Fragments and Culture Conditions.

After immersion in ethanol for 30 minutes the meteorite samples have been removed from alcohol and further manipulated with sterile forceps under a laminar flow sterile hood. Ethanol has been removed from the samples by flaming under the hood, where thereafter have been kept for 5 more minutes in the flame of a Bunsen burner holding them with sterile Klemmer forceps. From these samples there have been obtained fragments by scraping their surface with the needle of a sterile syringe for injections, further sterilized in the flame at red heat, changing syringes for each sample and experiment. The scraping of the sample surface has been performed also with nail file, using a new one, flame sterilized, for each experiments, Fragments of 1 mm diameter or smaller, have been collected directly on a layer of solid nutrient in a Petri dish 9.1 cm in diameter that has been immediately covered and sealed with parafilm under sterile hood and then kept at laboratory temperature. The culture medium was LB-agar. Stereo-microscope observations in the sealed Petri dishes were performed at 30 enlargements under tangent light illumination. The photographs have been taken with a digital camera.

Spectroscopic Analyses:

Spectra in visible and infrared light have been taken respectively with a Zeiss micro spectrophotometer and with a Perkin Elmer instrument. Photographs under fluorescent light were taken with a Nikon microscope Eclipse E 1000 equipped with digital camera DMX 1200. Fluorescence labelling has been performed with the live/dead BacLight kit of the Molecular Probes.

Scanning Electron Microscopy:

Analyses at the SEM have been performed with standard procedures using a microscope Cambridge 250 Mark 3. The EDS analyses (electronic energy dispersion of X rays) with a microscope Jeol 5310 linked to EDS link AN 10.000 Pentafet. Samples for only morphological observations were covered with gold while those for EDS analyses were not covered.

Gas-Chromatography, Mass-Spectrometry:

Analyses have been made with standard methods for monosaccharides and their derivatives after acetylation and trimethylsilinization using a GC-Mass 5390sd quadruple mass spectrometer (Agilent Technologies) equipped with a Hewlett-Packard gas chromatograph.

What is claimed is:

1. A method for providing non-living organic, metallorganic or biological material using a sample of metamorphic, igneous, sedimentary, or mineral rock, derived from chondrites, octahedrites, enstatitic olivines, or rock of similar origin comprising the following steps:
   providing a rock from which a fragment is to be obtained, the rock characterized by a first exposed surface prior to obtaining the fragment;
   heating the rock in a sterilizing temperature range for at least 5 minutes to provide a sterilized sample of the rock along the first exposed surface extending to a depth below the first exposed surface;
   removing a portion of the sterilized sample by obtaining a fragment from only a portion of the sterilized sample extending from the sterilized first exposed surface to the depth below the first exposed surface in a sterile atmosphere, by scraping or excavating with a needle or any other suitable acuminated tools;
   putting the fragment on a previously sterilized solid growth medium made of hydrolysates of natural products or synthetic derivatives thereof in the presence of oxygen at room temperature;
   incubating the fragment on the solid growth medium in the complete absence of living material for a desired incubation time; and
   when material consisting entirely of non-living material is generated on a surface of the fragment during or after the step of incubating, isolating the non-living material from the solid nutrient medium and optionally further analyzing it, wherein the step of incubating consists only of growing the fragment on the solid growth medium.

2. The method according to claim 1 wherein the sterilization step is performed by dipping the sample in ethyl alcohol for at least 20 minutes and further treatment on the direct flame of a burner for at least 5 minutes and/or in an autoclave for a period of 30 minutes to two hours, in whatever order.

3. The method according to claim 2 wherein the solid medium comprises tryptone, yeast extract and agar or gelrite.

4. The method according to claim 2, in which the generation of the material on the surface of the fragment proceeds through a phase of development in which the material is organized in globular, vesicular structures containing a fluid and a subsequent phase of quiescence in which the material is organized in opened or closed globular rigid structures.

5. The method according to claim 1, in which the rock sample is iperstenic or enstatitic chondrite.

6. A method for providing non-living organic, metallorganic or biological material using a sample of metamorphic, igneous, sedimentary, or mineral rock, derived from chondrites, octahedrites, enstatitic olivines, or rock of similar origin comprising the following steps:
   providing a rock from which a fragment is to be obtained, the rock characterized by a first exposed surface prior to obtaining the fragment;
   heating the rock in a sterilizing temperature range for at least 5 minutes to provide a sterilized sample of the rock along the first exposed surface extending to a depth below the first exposed surface;
   removing a portion of the sterilized sample by obtaining a fragment from only a portion of the sterilized sample extending from the sterilized first exposed surface to the depth below the first exposed surface in a sterile atmosphere, by scraping or excavating with a needle or any other suitable acuminated tool;
   putting the fragment on a previously sterilized solid growth medium made of hydrolysates of natural products or synthetic derivatives thereof in the presence of oxygen at room temperature;
   incubating the fragment on the solid growth medium to only to grow material consisting entirely of non-living material on a surface of the fragment; and
   after performing incubation to grow only material consisting entirely of the non-living material, isolating the grown non-living material from the solid medium.

* * * * *